United States Patent
Hasegawa (10) Patent No.: US 12,042,254 B2
(45) Date of Patent: Jul. 23, 2024

(54) PULSE RATE ESTIMATION METHOD, DEVICE, AND SYSTEM

(71) Applicant: Hitachi Kokusai Electric Inc., Tokyo (JP)

(72) Inventor: Keigo Hasegawa, Tokyo (JP)

(73) Assignee: HITACHI KOKUSAI ELECTRIC INC., Tokyo (JP)

( * ) Notice: Subject to any disclaimer, the term of this patent is extended or adjusted under 35 U.S.C. 154(b) by 290 days.

(21) Appl. No.: 17/638,798

(22) PCT Filed: Sep. 5, 2019

(86) PCT No.: PCT/JP2019/034939
§ 371 (c)(1),
(2) Date: Feb. 25, 2022

(87) PCT Pub. No.: WO2021/044571
PCT Pub. Date: Mar. 11, 2021

(65) Prior Publication Data
US 2022/0322950 A1    Oct. 13, 2022

(51) Int. Cl.
*A61B 5/024* (2006.01)
*A61B 5/00* (2006.01)

(52) U.S. Cl.
CPC ............ *A61B 5/024* (2013.01); *A61B 5/0077* (2013.01); *A61B 5/7203* (2013.01); *A61B 5/742* (2013.01)

(58) Field of Classification Search
CPC ..... A61B 5/024; A61B 5/0077; A61B 5/7203; A61B 5/742; A61B 5/02416; A61B 5/02438; A61B 5/6898; A61B 5/7214
See application file for complete search history.

(56) References Cited

U.S. PATENT DOCUMENTS

| | | | | |
|---|---|---|---|---|
| 2008/0249423 | A1* | 10/2008 | Kitajima | A61B 5/6826 600/500 |
| 2014/0073967 | A1* | 3/2014 | Engelbrecht | A61B 5/72 600/479 |

(Continued)

FOREIGN PATENT DOCUMENTS

| | | |
|---|---|---|
| JP | 2002-017694 A | 1/2002 |
| JP | 2008-253579 A | 10/2008 |

(Continued)

OTHER PUBLICATIONS

Yukihiro Kamiya, "A Simple Parameter Estimation Method for Periodic Signals Applicable to Vital Sensing Using Doppler Sensors," SICE Journal of Control, Measurement, and System Integration, 2017, vol. 10, Issue 5, pp. 378-384, Sep. 2017, DOI: https://doi.org/10.9746/jcmsi.10.378.

(Continued)

*Primary Examiner* — Hien N Nguyen
(74) *Attorney, Agent, or Firm* — PROCOPIO, CORY, HARGREAVES & SAVITCH LLP (57) ABSTRACT

Provided is a method for estimating a pulse rate with high accuracy in the case that short-term burst noise is mixed in an estimation interval. Included are a pulse wave signal generating step of generating a pulse wave signal from an image of a pulse rate estimation target; a peak component suppression step of limiting an amplitude value of the pulse wave signal that is larger than a first threshold value to the first threshold value, and outputting a pulse wave analysis signal; and a frequency analysis step of outputting a frequency spectrum of the pulse wave analysis signal.

7 Claims, 5 Drawing Sheets

(56) References Cited

U.S. PATENT DOCUMENTS

| | | | |
|---|---|---|---|
| 2014/0364750 A1* | 12/2014 | Brumfield | A61B 5/02455 600/500 |
| 2017/0086752 A1 | 3/2017 | Baxi et al. | |
| 2017/0086755 A1* | 3/2017 | De Haan | A61B 5/7278 |
| 2017/0340289 A1* | 11/2017 | Lin | A61B 5/7257 |
| 2018/0092556 A1 | 4/2018 | Ishiguro et al. | |
| 2018/0263514 A1* | 9/2018 | Hayase | A61B 5/02116 |
| 2018/0279957 A1 | 10/2018 | Jinnouchi | |
| 2019/0150834 A1* | 5/2019 | Zuckerman-Stark | A61N 1/36071 |
| 2020/0367784 A1* | 11/2020 | Cho | G01S 7/2923 |

FOREIGN PATENT DOCUMENTS

| | | |
|---|---|---|
| JP | 2009-112625 A | 5/2009 |
| JP | 2015-083101 A | 4/2015 |
| JP | 2015-205050 A | 11/2015 |
| JP | 2017-158675 A | 9/2017 |
| JP | 2018-166883 A | 11/2018 |
| JP | 2019-042145 A | 3/2019 |
| WO | 2016/167202 A1 | 10/2016 |

OTHER PUBLICATIONS

Daniel McDuff, Sarah Gontarek, and Rosalind W. Picard, "Improvements in Remote Cardio-Pulmonary Measurement Using a Five Band Digital Camera," IEEE Trans. Biomedical Engineering, vol. 61, No. 10, Oct. 2014.

Q. Zhang, Y. Zhou, S. Song, G. Liang and H. Ni, "Heart Rate Extraction Based on Near-Infrared Camera: Towards Driver State Monitoring," in IEEE Access, vol. 6, pp. 33076-33087, 2018.

English translation of the International Search Report dated Nov. 19, 2019, Issued in counterpart International Application No. PCT/JP2019/034939.

\* cited by examiner

Pulse Wave Signal s1: Amplitude 1, 1Hz
Noise Signal s2: Amplitude 5, 3Hz

FIG. 6

PULSE RATE ESTIMATION METHOD, DEVICE, AND SYSTEM

CROSS-REFERENCE TO RELATED APPLICATIONS

This application is US National Stage of International Patent Application PCT/JP2019/034939, filed Sep. 5, 2019, the contents of which are incorporated herein by reference.

TECHNICAL FIELD

The present invention relates to a pulse rate estimation method, device and system.

BACKGROUND OF THE INVENTION

Conventionally, as methods for estimating pulse rates, methods using electrocardiographs or pulse oximeters have been used in the medical and healthcare fields. In recent years, a wristwatch-type device for estimating pulse rates, called a smart watch, has come to be used.

However, these devices require the measurement device to be attached to the chest, wrist, finger, or the like of the subject, such that subjects may have their behavior restricted or feel uncomfortable wearing the device.

For this reason, as a simpler measurement method, a technique for estimating pulse rates without contact has been developed.

Patent Documents 1 to 3 propose a method of extracting information regarding a pulse wave from a skin image of a face or a hand as a time-series waveform (a pulse wave signal) and estimating the pulse rate from the waveform by FFT or the like. Technologies have been developed to reduce the effects of estimation errors due to changes in light sources or body movements. Further, Non-Patent Document 1 proposes an estimation method having a smaller amount of calculation than FFT as a method of extracting a pulse wave signal using a microwave radar and estimating the period of the waveform.

Patent Document 1 proposes a method of synthesizing signals of each wavelength of RGB by weighting the signals based on an estimated signal-to-noise ratio. This method aims to extract pulse wave signals with less noise.

In Patent Document 2, in order to compensate for body movement or the like, a method has been proposed in which a pulse wave signal extracted when body movements are small using information from a gyro sensor is used as a reference signal, and when the similarity with the signal is low, data is excluded from the pulse wave data and estimation is performed. However, this method requires a gyro sensor in addition to a camera to generate the reference waveform.

Patent Document 3 proposes a method of using the peak interval of the pulse wave signal and the fluctuation amount and dispersion of the peak value as features, and estimating a pulse rate only when the pulse rate is within a reference value. In addition, a method has been proposed in which a signal pattern is stored in advance as another reference, and the pulse rate is estimated only when the degree of similarity to the stored pattern is within the range of the reference. However, this document does not explicitly describe the method of setting the reference value.

Non-Patent Document 1 focuses on a method for detecting a low frequency signal, and describes a method (the author of this document calls it "ARS") for estimating the pulse rate from the intensity of signals having different cycles for each sample without performing a large-scale calculation such as FFT.

CITATION LIST

Patent Documents

[Patent Document 1] Japanese Unexamined Patent Application Publication No. 2015-83101 A
[Patent Document 2] Japanese Unexamined Patent Application Publication No. 2015-205050 A
[Patent Document 3] Japanese Unexamined Patent Application Publication No. 2017-158675 A

Non-Patent Documents

[Non-Patent Document 1] Yukihiro KAMIYA, "A Simple Parameter Estimation Method for Periodic Signals Applicable to Vital Sensing Using Doppler Sensors," SICE Journal of Control, Measurement, and System Integration, 2017, Volume 10, Issue 5, Pages 378-384, September 2017, DOI: https://doi.org/10.9746/jcmsi.10.378.
[Non-Patent Document 2] Daniel McDuff, Sarah Gontarek, and Rosalind W. Picard, "Improvements in Remote Cardio-Pulmonary Measurement Using a Five Band Digital Camera," IEEE Trans. Biomedical Engineering, vol. 61, no. 10, October 2014.
[Non-Patent Document 3] Q. Zhang, Y. Zhou, S. Song, G. Liang and H. Ni, "Heart Rate Extraction Based on Near-Infrared Camera: Towards Driver State Monitoring," in IEEE Access, vol. 6, pp. 33076-33087, 2018.

SUMMARY OF INVENTION

Technical Problem

As described above, non-contact type pulse rate estimation techniques have been developed from the viewpoints of methods for extracting pulse wave signals with less noise, performing estimation using sections having less noise, and speeding up processing.
However, although Patent Document 3 excludes noisy sections from the estimation sections (the sections to be used for estimation) using statistics, there is a problem in that it is difficult to perform exclusion using this method when the noisy section is a short (instantaneous) period. In addition, since a fluctuation due to body motion or the like generally has a large influence on waveforms, in the case that the pulse rate is estimated by FFT or the method of Non-Patent Document 1, this fluctuation appears as a large energy component, which may cause estimation errors. That is, there is a possibility that body movement cycles are estimated as a pulse.

Accordingly, the present invention provides a method of estimating pulse rates with high accuracy that is particularly suitable in cases that short-term burst noise is mixed into estimation sections.

Means for Solving the Problems

In order to solve the above problems, one representative pulse rate estimation method according to the present invention includes a peak component suppression step of limiting an amplitude value of the pulse wave signal that is larger than a first threshold value to the first threshold value, and outputting a pulse wave analysis signal; and a frequency analysis step of outputting a frequency spectrum of the pulse wave analysis signal.

Advantageous Effects of Invention

According to the present invention, it is possible to estimate a pulse rate with high accuracy in the case that short-term burst noise is mixed in estimation sections. Other problems, configurations and effects other than those described above will be made clear by the description of the following embodiments.

DESCRIPTION OF EMBODIMENT(S)

Hereinafter, embodiments of the present invention will be described with reference to the drawings. It should be noted that the present invention is not limited to these embodiments. Further, in the description of the drawings, the same portions are denoted by the same reference numerals.

Embodiments of the present invention will be described below with reference to the drawings.

Figure 1:
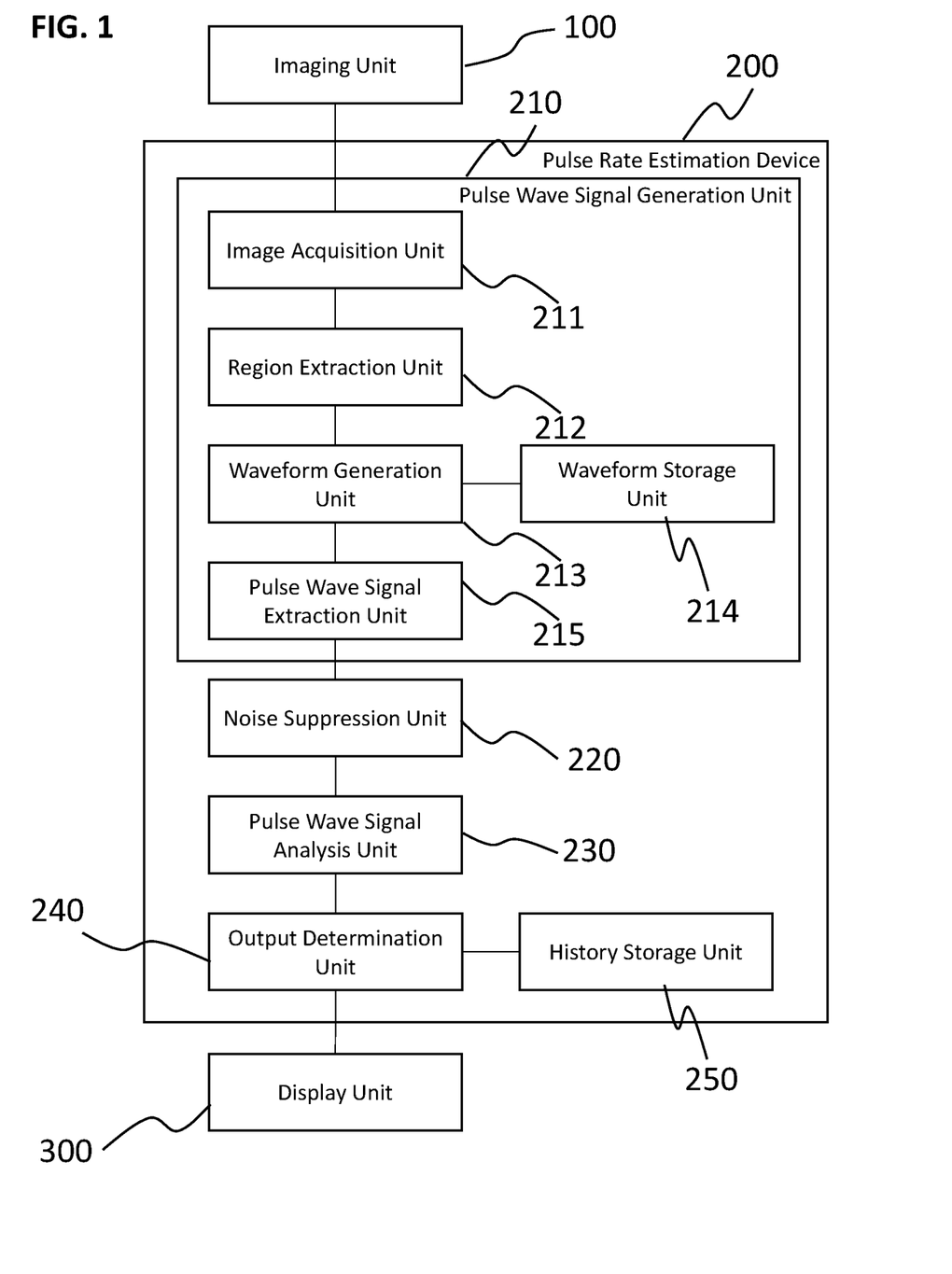
FIG. 1 is a functional block diagram of a pulse rate estimation system according to the embodiments of the present invention.
Figure 2:
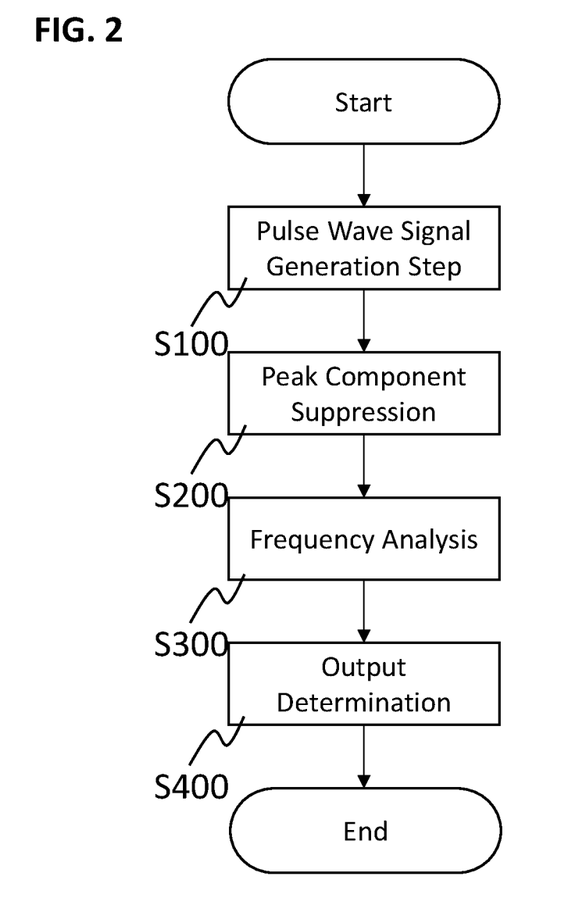
FIG. 2 is a flow chart of a pulse rate estimation process of the pulse rate estimation device illustrated in FIG. 1.

FIG. 1 is a functional block diagram of a pulse rate estimation system according to the embodiments of the present invention, and FIG. 2 is a flow chart of the pulse rate estimation process of the pulse rate estimation device 200 illustrated in FIG. 1.

The pulse rate estimation system includes an imaging unit 100, a pulse rate estimation device 200, and a display unit 300. The imaging unit 100 is an image capture device realized by an image sensor such as a CMOS or CCD, has a function of acquiring an image of a pulse rate estimation target, and may be, for example, a camera mounted on a smartphone or a notebook computer, a surveillance camera, a home video camera or the like. The pulse rate estimation device 200 is a device for estimating a pulse rate from the acquired image, and is realized by a computing processor such as a CPU, GPU, FPGA, or the like mounted in a personal computer, a smartphone, or the like. The display unit 300 has a function for displaying an estimation result of the pulse rate, an alert based on the estimation result, or the like, and is realized by a liquid crystal display or the like. In the present embodiment, a display example using a liquid crystal display is illustrated, but voice notification may be performed by a speaker. In addition, the estimation result of the pulse rate may be saved on a hard disk in the personal computer or in a cloud, and may be used as data for statistical analysis.

The pulse rate estimation device 200 includes a pulse wave signal generation unit 210, a noise suppression unit 220, a pulse wave signal analysis unit 230, an output determination unit 240 and a history storage unit 250. The pulse wave signal generation unit 210 generates a pulse wave signal from an image of a pulse rate estimation target, and includes an image acquisition unit 211, a region extraction unit 212, a waveform generation unit 213, a waveform storage unit 214 and a pulse wave signal extraction unit 215.

Figure 3:
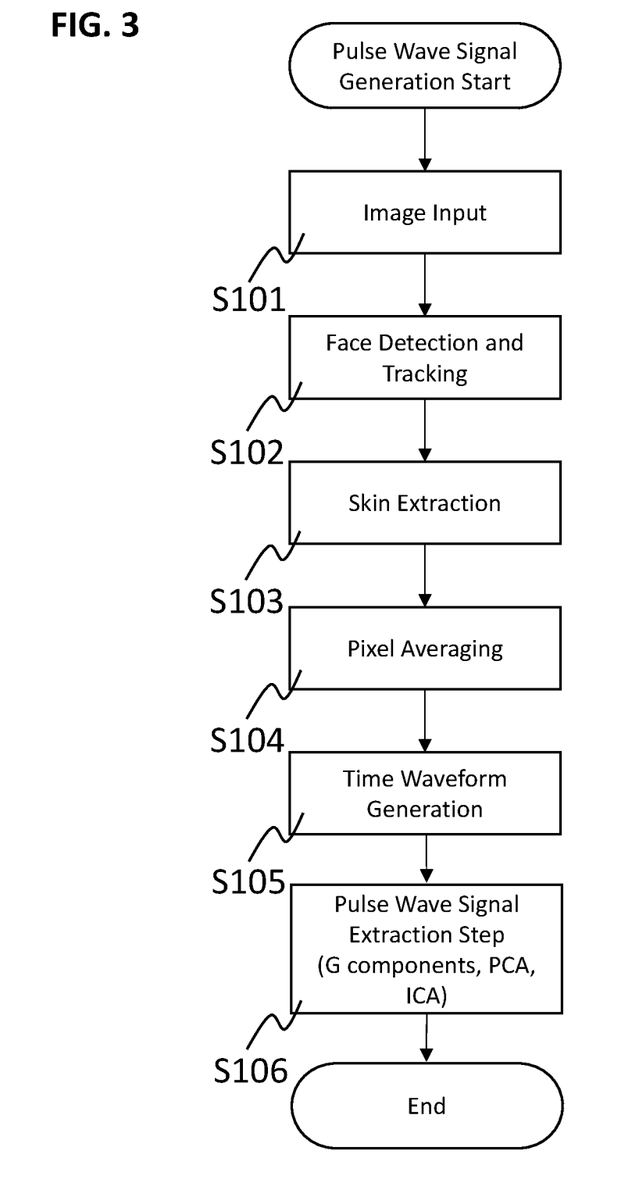
FIG. 3 is a flow diagram of the pulse signal generation step illustrated in FIG. 2.
Figure 4:
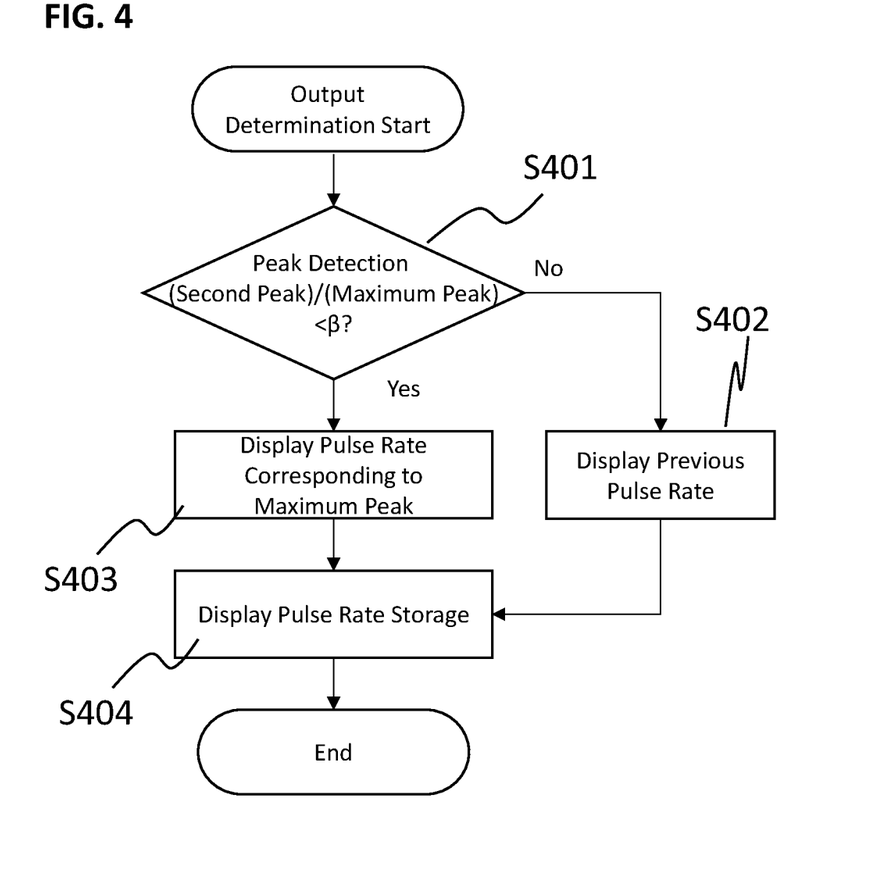
FIG. 4 is a flowchart of the output determination step illustrated in FIG. 2.

Next, a pulse rate estimation process in the pulse rate estimation device 200 will be described with reference to FIG. 2 to FIG. 4.

The pulse rate estimation process includes a pulse wave signal generation step S100, a peak component suppression step S200, a frequency analysis step S300, and an output determination step S400. The pulse wave signal generation step S100 generates a pulse wave signal from an image of the pulse rate estimation target, and includes an image input step S101, a face detection and tracking step S102, a skin extraction step S103, a pixel value averaging step S104, a time waveform generation step S105 and a pulse wave signal extraction step S106. The output determination step S400 outputs, as the pulse rate, a frequency at which a maximum peak value is obtained when the ratio of the second largest peak value to the maximum peak value of the frequency spectrum (in the case of decibels, the difference between the maximum peak value and the second largest peak value) is less than a second threshold value, and includes a peak detection step S401, a previous pulse rate display step S402, a pulse rate display step S403, and a display pulse rate storage step S404.

(S101: Image Input Step) The pulse rate estimation device 200 receives a video signal obtained from the imaging unit 100 by the image acquisition unit 211. In the present embodiment, an example of an image sensor capable of sensing an RGB spectrum is shown, but video signals may be generated by sensors that can sense spectra such as C (cyan), O (orange), and near infrared rays as described in Non-Patent Document 2 (an example of a five-band RGBCO camera), and Non-Patent Document 3 (an example of a near-infrared camera).

(S102: Face Detection/Tracking Step, S103 Skin Extraction Step) The region extraction unit 212 analyzes the received video signal, detects a face region, and then extracts a region (pixels) including the skin to be detected. Since video signals are sequentially sent from the imaging unit 100, the tracking processing of the face area is also performed so as to correspond to the movement of the face. In the present embodiment, a pulse rate estimation process using a face image is described, but the pulse rate estimation process may be performed on, for example, a palm, a neck, or the like, and may be performed on any region where skin is exposed.

(S104: Pixel Value Averaging Step, S105: Temporal Waveform Generation Step) The waveform generation unit 213 calculates the average value of the pixel values of the skin regions detected for each of the R (red), G (green), and B (blue) components, and stores the average value in the waveform storage unit 214. The waveform storage unit 214 stores the pixel values in chronological order, and can generate a time-series waveform by sequentially reading them out.

(S106: Pulse Wave Signal Extraction Step) The pulse wave signal extraction unit 215 extracts a component corresponding to the pulse wave signal from the time series waveform. A variety of extraction methods have been proposed, including those that use only the G components, those that perform independent component analysis (ICA), those that perform principal component analysis (PCA), and synthesis methods based on SNR (signal-to-noise power ratio) for RGB. It should be noted that, in the processing before and after the extraction of the pulse wave signal, the accuracy of the signal to be extracted may be improved by correction of the sampling interval, a bandpass filter (BPF), or the like.

Figure 5:
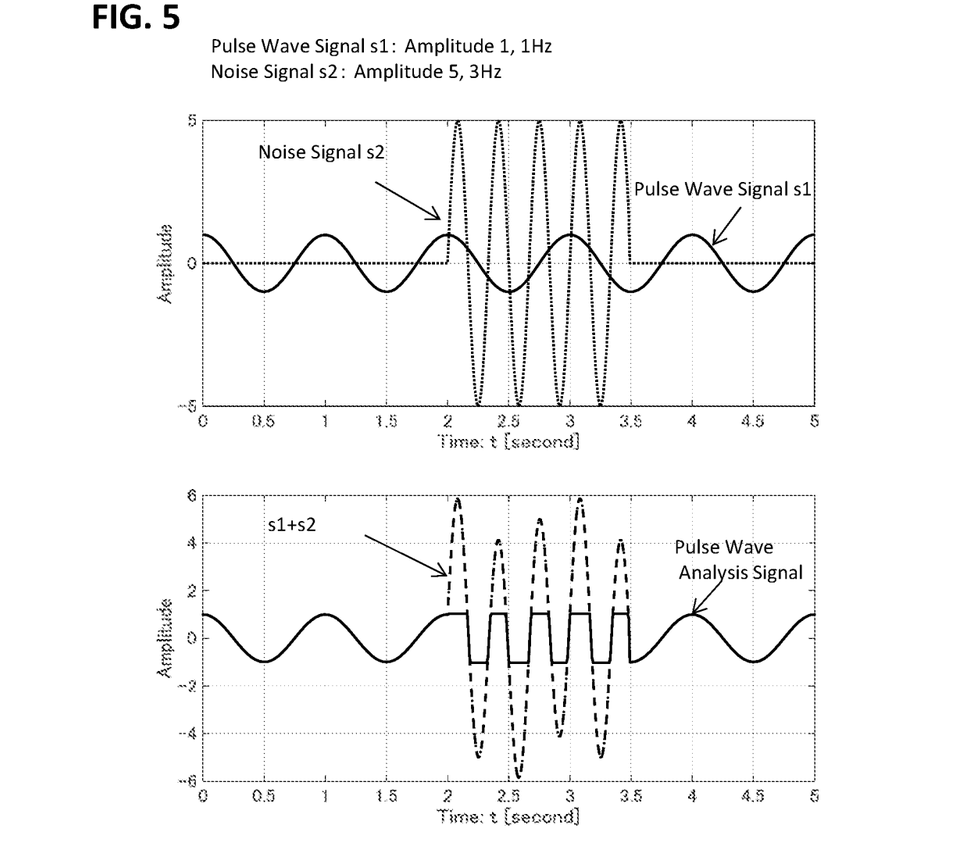
FIG. 5 is a conceptual diagram of a signal $s_1+s_2$ in a case that burst noise $s_2$ is mixed in a pulse wave signal Si and a signal (a pulse wave analysis signal) whose amplitude is limited to a threshold value $\alpha$.

(S200: Peak Component Suppression Step) In order to eliminate burst noise caused by body movements and changes in the light source, the noise suppression unit 220 limits the amplitude values of pulse wave signals that are larger than a first threshold value α to the first threshold value α and outputs the pulse wave analysis signal. FIG. 5 is a conceptual diagram of a signal $s_1+s_2$ in a case that burst noise $s_2$ is mixed in a pulse wave signal $s_1$ and a signal whose amplitude is limited to a threshold value α. In this example, the results are shown for a case in which a standard deviation σ of the amplitude value of the signal between time t=0 seconds and t=5 seconds is used and where α=aΓ and a=0.5. In practice, when the signals occurring between time t=0 seconds and t=5 seconds are denoted as $s_1, s_2, \ldots, s_n$, statistically, σ represents the standard deviation of the amplitude values, and the first threshold value α defined by multiplying the standard deviation by coefficient a (α=aσ) signifies an indicator of how much of the upper proportion, exceeding α, to be suppressed (cut) among different amplitudes distributing from the mean value (s). The standard deviation coefficient a may be set to an arbitrary positive value. The larger the value, the smaller the suppression effect of the noise $s_2$, and the smaller the value, the greater the suppression effect of the noise $s_2$, and at the same time, an effect of suppressing the pulse wave signal $s_1$ is also achieved. Accordingly, it is desirable to make adjustments before starting operation of the equipment.

Figure 6:
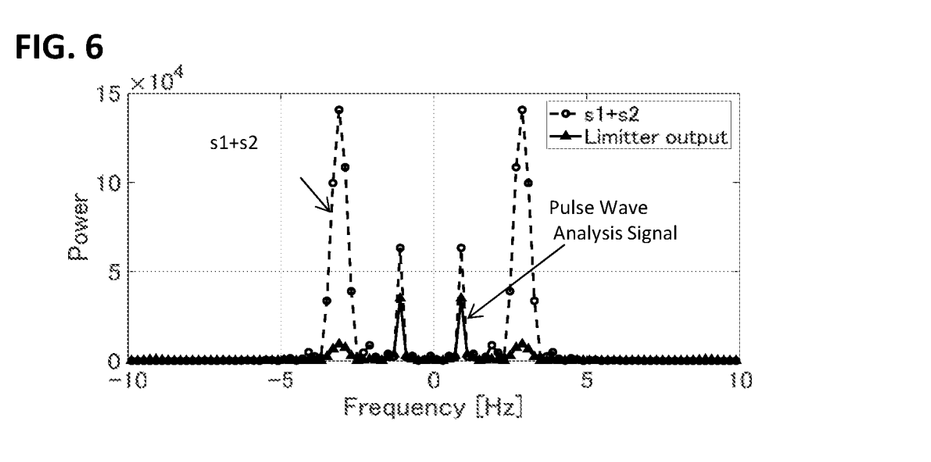
FIG. 6 is a frequency spectrum of $s_1+s_2$ and the pulse wave analysis signal illustrated in FIG. 5.

(S300: Frequency Analysis Step) The pulse wave signal analysis unit 230 performs a fast Fourier transform (FFT) with respect to the pulse wave analysis signal and outputs a signal energy (frequency spectrum) for each frequency. The frequency spectrum may be derived by using a plurality of bandpass filters having different pass bands, or by using a periodic signal extraction process corresponding to the bandpass filter as described in Non-Patent Document 1. FIG. 6 illustrates the frequency spectrum of $s_1+s_2$ of FIG. 5 and the pulse wave analysis signal. As illustrated in the figure, the pulse wave analysis signal has a spectrum in which the pulse wave signal has the maximum energy due to the effect of the noise suppression unit 220, and the pulse rate can be accurately estimated. Further, when the noise is small, the amplitude of the pulse wave signal in the sections where noise is not present is also limited, but since the energy of the pulse wave analysis signal is mainly due to the pulse wave signal, this is not problematic.

(S401: Peak Detection Step, S402: Previous Pulse Rate Display Step, S403: Pulse Rate Display Step, S404: Display Pulse Rate Storage Step) The output determination unit 240 detects the peak of the frequency spectrum. Further, the relationship between the maximum peak $p_1$ and the second peak $p_2$ (the second largest peak) is compared. In the case that $p_2/p_1<\beta$, it is assumed that the frequency $f_{p1}$ having the maximum peak corresponds to the pulse wave, and $60f_{p1}$ is displayed on the display unit 300 as the pulse rate. In the case that noise occurs, multiple large peaks appear, such that measurement cannot be performed accurately. Accordingly, when $p_2/p_1\geq\beta$, the pulse rate is not estimated, and the previously displayed pulse rate is displayed on the display unit 300. The second threshold value β may be set to an arbitrary value in the range of $0\leq\beta\leq1$, and the displayed pulse rate is stored in the history storage unit 250.

Although the embodiments of the present invention have been described above, the present invention is not limited to the above-described embodiments, and various modifications can be made without departing from the essence of the present invention. For example, although the above-described embodiment relates to non-contact type pulse rate estimation using a camera image, the present invention can be applied to pulse rate estimation using radar as well as other periodic signal estimation.

When the pulse rate estimation device 200 is realized by a computer processor such as a CPU, a GPU, or a FPGA mounted in a personal computer or a smart phone as in the above-described embodiments, programs for causing the computer to execute the above-described pulse rate estimation processing are also within the scope of the present disclosure.

REFERENCE SIGNS LIST

100: Imaging unit, 200: Pulse rate estimation device, 210: Pulse wave signal generation unit, 211: Image acquisition unit, 212: Region extraction unit, 213: Waveform generation unit, 214: Waveform storage unit, 215: Pulse wave signal extraction unit, 220: Noise suppression unit, 230: Pulse wave signal analysis unit, 240: Output determination unit, 250: History storage unit, 300: Display unit, S100: Pulse wave signal generation step, S101: Image input step, S102: Face detection and tracking step, S103: Skin extraction step, S104: Pixel value averaging step, S105: Time waveform generation step, S106: Pulse wave signal extraction step, S200: Peak component suppression step, S300: Frequency analysis step, S400: Output determination step, S401: Peak detection step, S402: Previous pulse rate display step, S403: Pulse rate display step, 5S04: Display pulse rate storage step, $s_1$: Pulse wave signal, $s_2$: Noise signal

The invention claimed is:

1. A pulse rate estimation method comprising:
   implementing a processor of a computer to perform:
   a pulse wave signal generating step of generating a pulse wave signal from an image of a pulse rate estimation target which is supplied by a non-contact type image sensor;
   a peak component suppression step of limiting an amplitude value of the pulse wave signal that is larger than a first threshold value to the first threshold value, and outputting a pulse wave analysis signal;
   a frequency analysis step of outputting a frequency spectrum of the pulse wave analysis signal by using a fast Fourier transform, a plurality of bandpass filters, or a periodic signal extraction process; and
   an output determination step of outputting, as a pulse rate, a frequency at which a maximum peak value is obtained when a ratio of a second largest peak value to a maximum peak value of the frequency spectrum is less than a second threshold value, otherwise a frequency displayed previously.

2. A pulse rate estimation method comprising:
   implementing a processor of a computer to perform:
   a pulse wave signal generating step of generating a pulse wave signal from an image of a pulse rate estimation target which is supplied by a non-contact type image sensor;

a peak component suppression step of limiting an amplitude value of the pulse wave signal that is larger than a first threshold value to the first threshold value, wherein a feature of a waveform of the pulse wave signal is extracted, and a sample value of the pulse wave signal that has a large amplitude outside a range of the first threshold value calculated based on the feature of the waveform is replaced with the first threshold value, and outputting a pulse wave analysis signal:

a frequency analysis step of outputting a frequency spectrum of the pulse wave analysis signal by using a fast Fourier transform, a plurality of bandpass filters, or a periodic signal extraction process; and an output determination step of outputting, as a pulse rate, a frequency at which a maximum peak value is obtained when a ratio of a second largest peak value to a maximum peak value of the frequency spectrum is less than a second threshold value, otherwise a frequency displayed previously.

3. The pulse rate estimation method of claim 2, wherein the feature of the waveform is a standard deviation.

4. A pulse rate estimation device comprising:
implementing a processor of a computer to perform:
a pulse wave signal generation unit for generating a pulse wave signal from an image of a pulse rate estimation target which is supplied by a non-contact type image sensor;

a noise suppression unit for limiting an amplitude value of the pulse wave signal that is larger than a first threshold value to the first threshold value, and outputting a pulse wave analysis signal;

a pulse wave signal analysis unit for outputting a frequency spectrum of the pulse wave analysis signal by using a fast Fourier transform, a plurality of bandpass filters, or a periodic signal extraction process; and an output determination unit for outputting, as a pulse rate, a frequency at which a maximum peak value is obtained when a ratio of a second largest peak value to a maximum peak value of the frequency spectrum is less than a second threshold value, otherwise a frequency displayed previously.

5. The pulse rate estimation device according to claim 4, wherein the noise suppression unit extracts a feature of a waveform of the pulse wave signal, and replaces a sample value of the pulse wave signal that has a large amplitude outside a range of the first threshold value calculated based on the feature of the waveform with the first threshold value.

6. The pulse rate estimation device according to claim 5, wherein the feature of the waveform is a standard deviation.

7. A pulse rate estimation system comprising:
an imaging unit for supplying the image;
the pulse rate estimation device according to claim 4; and
a display unit for displaying an output pulse rate.

* * * * *